| United States Patent [19] | [11] Patent Number: 5,231,027 |
|---|---|
| Bianchi et al. | [45] Date of Patent: Jul. 27, 1993 |

[54] ENZYMATIC PROCESS FOR SEPARATING THE OPTICAL ISOMERS OF RACEMIC 1,2-DIOLS USING LIPASE

[75] Inventors: Daniele Bianchi, Milan; Aldo Bosetti, Vercelli; Pietro Cesti, Trecate; Paolo Golini, Milan; Sandro Spezia, Piacenza, all of Italy

[73] Assignee: Ministero Dell 'Universita' E Della Ricerca Scientifica E. Technologica, Rome, Italy

[21] Appl. No.: 755,048

[22] Filed: Sep. 5, 1991

[30] Foreign Application Priority Data

Sep. 7, 1990 [IT] Italy ................. 21404 A/90

[51] Int. Cl.$^5$ ................. C12P 7/62
[52] U.S. Cl. ................. 435/280; 435/135
[58] Field of Search ................. 435/280, 135

[56] References Cited

FOREIGN PATENT DOCUMENTS 77476 3/1988 Japan .

OTHER PUBLICATIONS

Okumura S., BBA 575:156-165 (1979).
Hills, M., BBA 1042:237-240 (1990).
Bianchi D., J Org Chem, 53:5531-34 (1988).
Cambou, B., Biotech and Bioeng. XXVI:1449-54 (1984).

*Primary Examiner*—Douglas W. Robinson
*Assistant Examiner*—S. Saucier
*Attorney, Agent, or Firm*—Oblon, Spivak, McClelland, Maier & Neustadt

[57] ABSTRACT

The optical isomers of racemic 1,2-diols are separated by enzymatic way, by means of a process involving the following operations:
reaction of the racemic mixture of the 1,2 diols with an organic anhydride in the presence of enzyme belonging to the class of lipases;
separation of the enzyme;
removal of the excess of anhydride;
separation of the produced esters, in optically pure form by column chromatography;
recovery of the 1,2 diols, as optically pure enantiomers.

13 Claims, No Drawings

ENZYMATIC PROCESS FOR SEPARATING THE OPTICAL ISOMERS OF RACEMIC 1,2-DIOLS USING LIPASE

The present invention relates to an essentially enzymatic process for separating the optical isomers of racemic 1,2-diols. The process involves the following basic operations:
- reaction of the racemic mixture of the 1,2 diols with an organic anhydride in the presence of a suitable enzyme;
- separation of the enzyme;
- removal of the excess of anhydride;
- separation of the so produced esters;
- hydrolysis of the esters and consequent restoration and recovery of the 1,2 diols, as optically pure enantiomers.

The present invention relates to a process for separating the optical isomers of 1,2-diols of formula

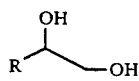  (I)

in which R represents the radical

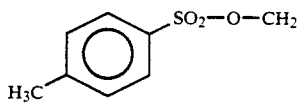  (II)

or the radical

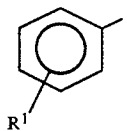  (III)

in which:
R$^1$ means hydrogen, or a linear or branched C$_1$-C$_8$ alkyl or alkenyl radical, or a C$_3$-C$_8$ cycloalkyl radical, or a C$_1$-C$_6$ alkoxy radical, or, an halogen or a nitro group.

The process consists in the reaction of the racemic mixture of the (1,2) diols with an acylating compound of formula (R''—CO)$_2$O  (IV)

in which:
R'' means a linear or branched C$_1$-C$_6$ alkyl group.
This process is carried out in the presence of an either free or immobilized enzyme, capable of catalysing the nonstereoselective esterification of the primary hydroxy group and the stereoselective esterification of the secondary hydroxy group, in the compounds of formula (I).

It is well-known that the mentioned (1,2)-diols, as pure enantiomers, are useful synthons in pharmaceutical and agro-alimentary sectors, e.g.:

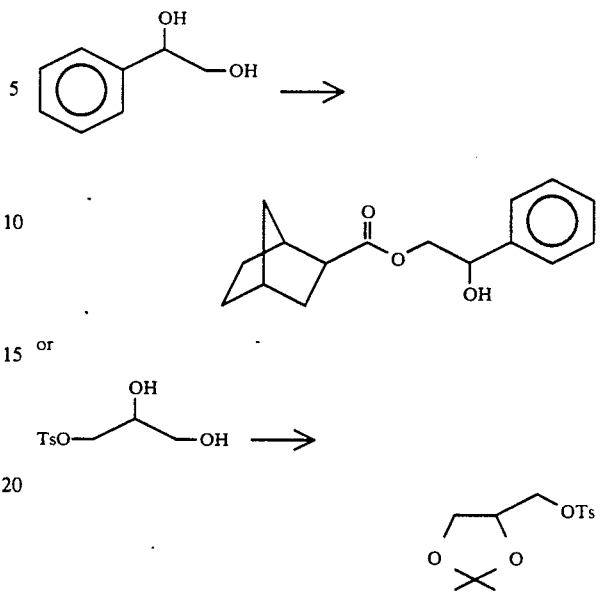

in which

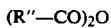

Several methods to produce (1,2) diols as pure emantiomers are described.

For example, (S)-1,2-phenylethandiol is obtained by chemical reduction of (S) mandelic acid; however, this method allows to prepare only one emantiomer [J.O.C. 44, 1729 (1979)].

Furthermore it's described the synthesis of the optically active diol in which R is represented by (II). The procedure utilizes (D)-mannitol, which is oxidized by lead tetra-acetate, into diglyceraldehyde acetonide.

The acetonide is further reduced by hydrides into isopropylideneglycerol, which is tosylated and deprotected in an acidic media.

This method is not suitable to be utilized in industrial production since it involves several sinthetic steps and the use of large amounts of lead tetraacetate [J.O.C. 43, 4876 (1978)].

A biochemical resolution of a mixture of the racemates of (1,2)-diols is disclosed in European patent application No. 317,998.

This process consists in submitting a mixture of both antipodes of 1,2-diols to the action of suitable microorganisms capable of selectively metabolizing the (R) form of such diols, leaving unreacted the (S) form.

However the method disclosed in the European patent applications as far as only low product isolation yields furthermore, only one optically active form could be obtained.

On the contrary, the present invention consists in a process to resolve the optical isomers of a racemic mixture of 1,2-diols represented in formula (I), which makes it possible to obtain both optically active forms in an easy, effective way, and with high yields.

The process consists essentially in a reaction of the racemic mixture of the (1,2)-diols of formula (I) an organic anhydride in the presence on an enzyme capable to catalyze the non-stereoselective esterification of the primary hydroxy group and the stereoselective esterification of the secondary hydroxy group.

Therefore, the present invention deals with a process for separating the optical isomers of 1,2-diols of formula

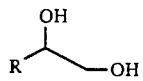  (I)

in which R represents the radical

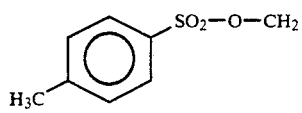  (II)

or the radical

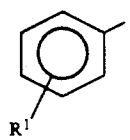  (III)

in which $R^1$ means hydrogen, or a linear or branched $C_1$-$C_8$ alkyl or alkenyl radical, or a $C_3$-$C_8$ cycloalkyl radical, or a $C_1$-$C_6$ alkoxy radical, or, an halogen or a nitro group.

This process consists in reacting the racemic mixture of the diols of formula (I) with an acylating agent of formula $$(R''-CO)_2O \qquad (IV)$$

in which $R''$ represents a linear or branched $C_1$-$C_6$ alkyl group, in the presence of an enzyme belonging to the class of lipases, separating the enzyme, removing the excess of acylating compound, separating the resulting esters, hydrolysing and consequently recovering the diols as optically pure enantiomers.

As further details of the present process, the racemic (1,2)-diols (formula (I)) react with an anhydride (formula VI) in an organic solvent, in the presence of an enzyme belonging to the class of lipases.

The reaction schemes are the following:

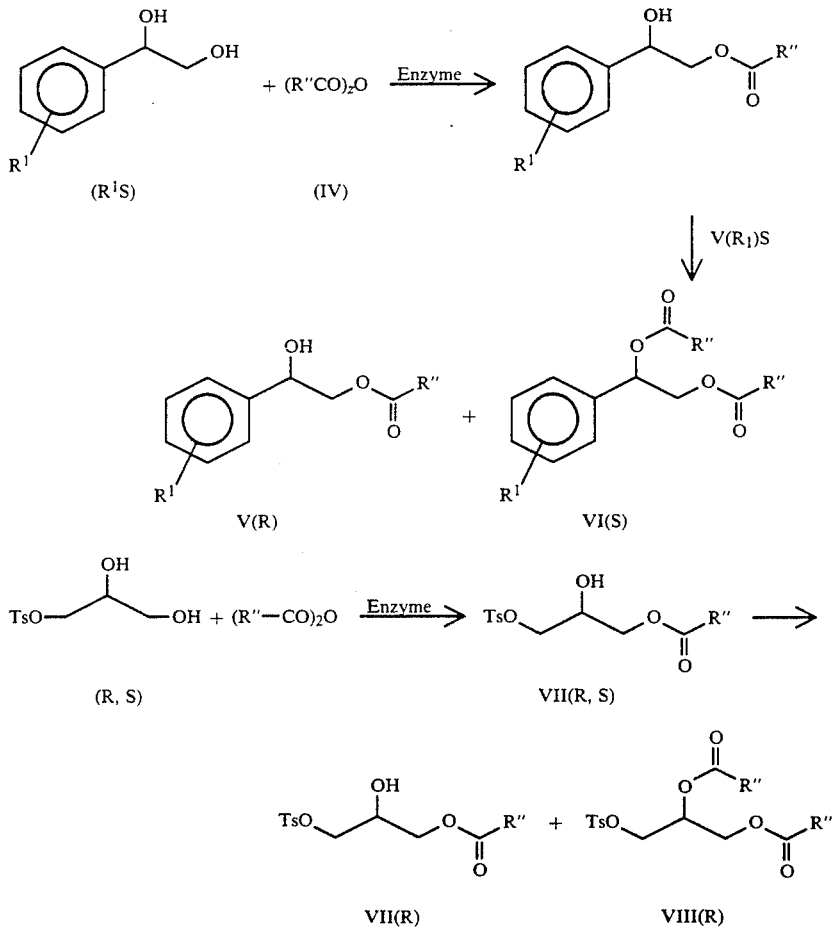

wherein the symbols $R'$, $R''$ have the above defined meanings.

The racemic 1,2-diols of formula (I), i.e., the starting compounds, are per se known and/or can be synthetized by conventional techniques.

The resulting esters of formula V(R), VI(S), VII(S) and VIII(R) can be subsequently separated by conventional techniques, (e.g., column chromatography).

Preferred anhydrides are acetic anhydride and propionic anhydride. The process is carried out in an organic solvent, preferably selected from the halogenated aliphatic hydrocarbons, (e.g., methylene chloride), and the tertiary aliphatic alcohols, (e.g., 2-methyl-butan2-ol).

In the reaction, molar ratios of anhydride (IV) to diols (I) are used, which are comprised within the range from 1.6:1 to 5:1, preferably from 2.5:1 to 3:1. The enzyme is used according to a weight ratio of the enzyme to the substrate of formula (I) comprised within the range from 1:1 to 1:100, preferably from 1:1 to 1:20.

Molar concentration, of the racemic diol (I) in the reaction mixture can be comprised within the range from 0.01M to 2M, preferably from 0.05M to 1M.

The esterification process is carried out by vigorously stirring the reaction mixture constituted by the compound (I), the reactant (IV), the solvent and the either free or supported enzyme, at temperatures comprised within the range from 0° C. to 50° C., preferably from 20° to 30° C.

When the reaction is over, the enzyme, constituting the solid phase, essentially can be recovered by filtration and re-used without substantial losses of activity.

From the filtrate, after removing the excess of anhydride (IV), e.g., by means of an aqueous solution of alkali-metal carbonate, the monoester(V) in (R) form is separated from the diester (VI) in (S) form; or the monoester (VII) in (S) form is separated from the diester (VIII) in (R) form by using traditional methods, such as, column chromatography.

The obtained esters can be transformed into the corresponding optically active (1,2)-diols of formula (I). by traditional chemical methods, (e.g., with methanol under reflux conditions).

The utilized enzymes according to the present invention belong to the class of lipases of microbial origin.

The following enzymes have proven to be particularly active:

| Enzyme | Manufacturer | Manufacturer |
| --- | --- | --- |
| LPL | *Pseudomonas aeruginosa* | Amano Pharm. Co (Japan) |
| Lipase P | *Pseudomonas fluorescens* | Amano Pharm. Co (Japan) |
| Lipase CES | *Pseudomonas spp.* | Amano Pharm. Co (Japan) |
| Lipase | Chromobacterium | Tojobo (Japan) |

According to the present invention, the enzymes can be used either free, or immobilized on suitable supports. The immobilization of the enzyme increase its activity and stability, and facilitate its recovery and re-use.

Porous supports with a high surface area, such as, Celite, porous glass, silica, and so forth, have shown to be particularly suitable for that purpose.

The immobilization can be easily obtained by stirring in a buffer solution the crude power of the enzyme with the choosen support. After filtration the, immobilized enzyme preparation is left to dry at room temperature.

Further details will be given in the following examples, illustrating the invention without limiting it.

EXAMPLE 1

Immobilization of the Enzyme 1.5 g of enzyme Lipase P (from Amano Pharm. Co. Ltd.'s *Pseudomonas fluorescens*, 30 units per mg), dissolved in 4 ml of 0.1M Na/K phosphate buffer solution, pH=7, is added to 5 g of Celite 577 (Johns-Manville Ltd., Richmond, Surrey).

The resulting mixture is mixed to obtain a uniform distribution of the enzyme, and then the immolized enzyme dried in air, at 25° C., for 24 hours.

Separation of the Enantiomers of 1,2-Phenylethanediol 1 g of Celite 577 containing 300 mg of immobilized Lipase P enzyme and 3.1 g of propionic anhydride are added to 1.5 g of (R,S)-1,2-phenylethanediol dissolved in 40 ml of 2-methyl-2-butanol.

The mixture is vigorously stirred at 25° C., and the reaction is monitored by gas-chromatography.

After 22 hours, the formation of 50% of diester and 50% of monoester of the primary hydroxy group has occurred. At this point, the enzyme is filtered off, the recovered organic phase is washed with a solution of sodium carbonate at 5%. The organic phase is dried on sodium sulfate, evaporated under reduced pressure and the residue is chromatographed on a silica-gel column, using an eluent consisting of a hexane:ethyl acetate mixture in the ratio of 90:10 volume/volume (=v/v).

We obtained 1,4 g of (S)-1,2-propanoyloxy-phenylethane, as a colourless oil, with $[\alpha]_D^{25} = +59.4$ (c=1, acetone), ee=91%, $^1$H-N.M.R. (200 MHz, CDCl$_3$), δ (ppm): 1.2 (6H, t), 2.4 (4H, q), 4.4 (2H, m), 6.1 (1H, m), 7.4 (5H, s); together with 1 g of (R)-1-propanoyloxy-2-phenylethanol, as a colourless oil, with $[\alpha]_D^{25} = -15.2$ (c=1, acetone), ee=60%, $^1$H-N.M.R. (200 MHz, CDCl$_3$), δ (ppm): 1.2 (3H, t), 2.4 (2H, q), 2.9 (1H, s), 4.2 (2H, m), 4.95 (1H, m), 7.4 (5H, s).

The compounds were converted onto the respective diols, by hydrolysis in methanol, and their enantiomeric excess were determined by HPLC (Chiralcel OC column, available from Daicel).

EXAMPLE 2

Separation of the Enantiomers of 4'-Chloro-1,2-phenylethanediol 2.5 g of Celite 577 containing 750 mg of immobilized Lipase P enzyme and 2.5 g of propionic anhydride are added to 1 g of (R,S)-4'-chloro-1,2-phenylethanediol dissolved in 25 ml of 2-methyl-2-butanol.

The mixture is vigorously stirred at 25° C., and the reaction is monitored by gas-chromatography.

After 22 hours, the formation of 50% of diester and 50% of monoester of the primary hydroxy group has occurred. At this point, the enzyme is filtered off, and the recovered organic phase is washed with a solution of sodium carbonate at 5%. The organic phase is dried on sodium sulfate, evaporated under reduced pressure and the residue is chromatographed on a silica-gel column, using an eluent consisting of a hexane:ethyl acetate mixture in the ratio of 90:10 (v/v).

We obtained 700 mg of (S)-4'-chloro-1,2-propanoyloxyphenylethane, as a colourless oil, with $[\alpha]_D^{25} = +57.5$ (c=1, acetone), ee=93%, $^1$H-N.M.R. (200 MHz, CDCl$_3$), δ(ppm): 1.1 (3H, t), 1.15 (3H, t), 2.3 (2H, q), 2.4 (2H, q), 4.3 (2H, m), 6 (1H, dd), 7.3 (4H, m); together with 600 mg of (R)-4'-chloro-1-propanoyloxy-2-phenylethanol, as a colourless oil, with $[\alpha]_D^{25} = -11.0$ (c=1, acetone), ee=80%, $^1$H-N.M.R. (200 MHz, CDCl$_3$), δ(ppm): 1.1 (3H, t), 2.35 (2H, q), 3 (1H, broad), 4.1 (2H, m), 4.95 (1H, dd), 7.3 (4H, m).

After transformation into 1,2-phenylethane-diol by catalytic dehydrogenation, such compounds were converted into the respective diols, by hydrolysis in methanol. Their enantiomeric excess and configuration were determined by HPLC (Chiralcel OC column, available from Daicel).

EXAMPLE 3

Separation of the Enantiomers of 4'-Nitro-1,2-phenylethanediol 2.75 g of Celite 577 containing 743 mg of immobilized Lipase P enzyme and 3 g of propionic anhydride are added to 1.28 g of (R,S)-4'-nitro-2-phenylethanediol dissolved in 28 ml of 2-methyl-2-butanol.

The mixture is vigorously stirred at 25° C., and the reaction is monitored by gas-chromatography.

After 3 hours, the formation of 33% of diester and 67% of monoester of the primary hydroxy group has occurred. At this point, the enzyme is filtered off, the recovered organic phase is washed with a solution of sodium carbonate at 5%. The organic phase is dried on sodium sulfate, evaporated under reduced pressure and then the residue is chromatographed on a silica-gel column, using an eluent consisting of a hexane:ethyl acetate mixture in the ratio of 80:20 (v/v).

We obtained 600 mg of (S)-4'-nitro-1,2-propanoyloxyphenylethane, with $[\alpha]_D^{25} = +43.6$ (c=1, acetone), ee=98%, $^1$H-N.M.R. (200 MHz, CDCl$_3$), $\delta$(ppm): 1.2 (6H, m), 2.4 (4H, m), 4.3 (2H, m), 6 (1H, t), 7.5 (2H, d), 8.2 (2H, d); together with 650 mg of (R)-4'-nitro-1-propanoyloxy-2-phenylethanol, as a colourless oil, with $[\alpha]_D^{25} = -5.8$ (c=1, acetone), ee=42.6%, $^1$H-N.M.R. (200 MHz, CDCl$_3$), $\delta$(ppm): 1.2 (3H, t), 2.4 (2H, q), 3 (1H, broad), 4.2 (2H, m), 5.0 (1H, m), 7.6 (2H, d); 8.2 (2H, d).

The obtained products were converted into 1,2-phenylethane-diol, by reduction of the nitro group to amino group, diazotization and subsequent reduction of the diazo derivative. This product was analyzed by an HPLC method (Chiralcel OC column, available from Daicel) to determine the enantiomeric excess.

EXAMPLE 4

Separation of the Enantiomers of 3-Tosyloxy-1,2-propanediol 5 g of Celite 577 containing 1.5 g of immobilized Lipase P enzyme and 10.8 g of propionic anhydride are added to 10 g of (R,S)-3-tosyloxy-1,2-propanediol dissolved in 250 ml of 2-methyl-2-butanol.

The mixture is vigorously stirred at 25° C., and the reaction is monitored by reverse-phase HPLC.

After 5 hours, the formation of 49% of diester and 51% of monoester of the primary hydroxy group has occurred. At this point, the enzyme is filtered off, the recovered organic phase is washed with a solution of sodium carbonate at 5%. The organic phase is dried on sodium sulfate, evaporated under reduced pressure and the residue is chromatographed on a silica-gel column, using an eluent consisting of a hexane:ethyl acetate mixture in the ratio of 80:20 (v/v).

In that way, we obtained 5.7 g of (S)-1-propanoyloxy-3-tosyloxy-2-propanol, as a colourless oil, with $[\alpha]_D^{25} = +3.7$ (c=1, acetone), ee=98%, $^1$H-N.M.R. (200 MHz, CDCl$_3$), $\delta$(ppm): 1.1 (3H, t), 2.3 (2H, q), 2.45 (3H, s), 4.1 (5H, m), 7.35 and 7.75 (4H, dd); together with 6.5 g of (R)-1,2-propanoyloxy-3-tosyloxy-propane, as a colourless oil, with $[\alpha]_D^{25} = +7.77$ (c=1, CHCl$_3$), ee=86%, $^1$H-N.M.R. (200 MHz, CDCl$_3$), $\delta$(ppm): 1.1 (6H, q), 2.3 (4H, q), 2.45 (3H, s), 4.15 (4H, m), 5.1 (1H, m), 7.35 and 7.75 (4H, dd).

The so obtained compounds were hydrolysed into their respective diols in gently refluxing methanol. The enantiomeric excess was determined by comparison with an optically pure sample of 3-tosyloxy-1,2-propanediol, obtained by traditional chemical methods.

We claim:

1. A process for separating the optical isomers of a 1,2-diol of formula (I)

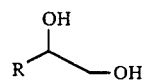

wherein R is a radical of formula (II)

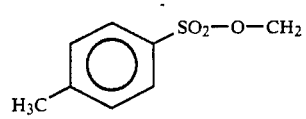

or a radical of formula (III)

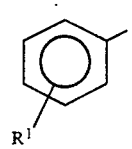

wherein R$^1$ is selected from the group consisting of hydrogen, linear or branched C$_1$-C$_8$ alkyl, linear or branched C$_2$-C$_8$ alkenyl, C$_3$-C$_8$ cycloalkyl, C$_1$-C$_6$ alkoxy, halogen and nitro, said process comprising: (i) reacting a racemic mixture of a (1,2)-diol of formula (I) with an acylating compound of formula (IV)

$$(R''-CO)_2O \qquad (IV)$$

wherein R'' is a linear or branched C$_1$-C$_6$ alkyl group, said reacting being catalyzed by an enzyme which is a lipase selected from the group consisting of LPL produced by Pseudomonas aeruginosa, Lipase P produced by Pseudomonas fluorescens, Lipase CES produced by Pseudomonas spp., and Lipase produced by Chromobacterium to obtain a mixture of esters of formulae (V) and (VI)

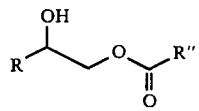

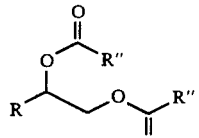

wherein R and R'' are defined above; recovering said enzyme; removing any excess of said acylating compound; separating said esters; and hydrolyzing said esters, wherein the reaction is carried out in an organic solvent.

2. The process of claim 1, wherein said organic solvent is selected from the group consisting of halogenated aliphatic hydrocarbons and aliphatic tertiary alcohols.

3. The process of claim 1, wherein the reacting is carried out with a molar ratio of said acylating agent to said diol of from 1.6:1 to 5:1.

4. The process of claim 3, wherein said molar ratio of said acylating agent to said diol is 2.5:1 to 3:1.

5. The process of claim 1, wherein said acylating agent is selected from the group consisting of acetic anhydride and propionic anhydride.

6. The process of claim 1, wherein the weight ratio of said enzyme to said diol is from 1:1 to 1:100.

7. The process of claim 6, wherein said weight ratio of said enzyme to said diol is from 1:1 to 1:20.

8. The process of claim 1, wherein said enzyme is immobilized.

9. The process of claim 1, wherein the reaction is carried out at a temperature of from 0° C. to 50° C.

10. The process of claim 9, wherein said temperature is from 20° C. to 30° C.

11. The process of claim 1, wherein the recovery of said enzyme is effected by filtration.

12. The process of claim 1, wherein the removal of excess of said acylating agent is carried out by adding an aqueous solution of alkali-metal carbonate.

13. The process of claim 1, wherein the hydrolysis of said esters is carried out in methanol.

* * * * *